(12) United States Patent
Sun (10) Patent No.: US 8,771,606 B2
(45) Date of Patent: Jul. 8, 2014

(54) KITCHEN WASTE BIN

(75) Inventor: Brian Sun, North Point (HK)

(73) Assignee: T Plus Limited, Hong Kong (HK)

( * ) Notice: Subject to any disclaimer, the term of this patent is extended or adjusted under 35 U.S.C. 154(b) by 571 days.

(21) Appl. No.: 12/840,620

(22) Filed: Jul. 21, 2010

(65) Prior Publication Data
US 2011/0020184 A1 Jan. 27, 2011

(30) Foreign Application Priority Data

Jul. 22, 2009 (GB) .................................. 0912689.7

(51) Int. Cl.
| | | |
|---|---|---|
| *A61L 9/00* | (2006.01) | |
| *G01N 23/00* | (2006.01) | |
| *A61N 5/00* | (2006.01) | |
| *B65D 83/10* | (2006.01) | |
| *B65D 25/00* | (2006.01) | |
| *B65F 1/14* | (2006.01) | |
| *B65F 1/08* | (2006.01) | |
| *B65F 7/00* | (2006.01) | |
| *A61L 2/10* | (2006.01) | |
| *A61L 2/20* | (2006.01) | |

(52) U.S. Cl.
CPC . *B65F 1/163* (2013.01); *B65F 1/08* (2013.01); *B65F 7/00* (2013.01); *A61L 2/10* (2013.01); *A61L 2/202* (2013.01)
USPC ... 422/305; 422/306; 250/455.11; 250/492.1; 206/362.1; 220/87.1

(58) Field of Classification Search
CPC ..... A01N 1/0294; A01N 1/0215; A61K 8/22; A61L 2/202; A61L 9/00; A61L 9/015; A61L 9/03; A61L 9/032; A61L 9/20
USPC .............. 422/24, 186, 186.3, 305–306; 250/455.11, 492.1; 206/362.1; 220/87.1
See application file for complete search history.

(56) References Cited

U.S. PATENT DOCUMENTS

| | | | |
|---|---|---|---|
| 6,365,113 | B1 | 4/2002 | Roberts |
| 2008/0175751 | A1 | 7/2008 | Sun et al. |

FOREIGN PATENT DOCUMENTS

| | | |
|---|---|---|
| CN | 2668568 Y | 1/2004 |
| DE | 10330837 | 2/2005 |

(Continued)

OTHER PUBLICATIONS

The Korean Intellectual Property Office English Translation of KR 10-2002-0017221.*

*Primary Examiner* — Monzer R Chorbaji
(74) *Attorney, Agent, or Firm* — Price Heneveld LLP (57) ABSTRACT

A kitchen waste bin having a casing; a lid hingedly attached to the casing and moveable between open and closed positions. The lid includes an outer casing, an inner casing and a cavity there between. The inner casing having one or more apertures communicating between the cavity and the interior of the receptacle when the lid is closed; an ozone generator located within the cavity arranged to discharge ozone into the receptacle where the ozone generator is an ultraviolet source that includes an elongate lamp in an elongate channel shaped reflector; a switch that generates and transmits a control signal when the lid is moved; and a control unit arranged to switch the ozone generator on or off in response to a control signal. Ozone is discharged into the receptacle for a sterilization period when the lid is closed. Discharge of the ozone stops when the lid is opened.

8 Claims, 4 Drawing Sheets

(56) References Cited

FOREIGN PATENT DOCUMENTS

| | | | | |
|---|---|---|---|---|
| EP | 1454849 | | 5/2006 | |
| GB | 2 403 397 A | * | 1/2005 | ............... B65F 1/14 |
| GB | 2403397 A | | 1/2005 | |
| JP | 10-109702 A | | 4/1998 | |
| KR | 10-2002-0017221 | * | 3/2002 | ............... B65F 1/00 |

* cited by examiner

KITCHEN WASTE BIN

CROSS REFERENCE TO RELATED APPLICATION

The present application claims priority to and the benefit of United Kingdom Application No. 0912689.7 filed on Jul. 22, 2009, under 35 U.S.C. §119. The entire disclosure of United Kingdom Application No. 0912689.7 is hereby incorporated by reference.

BACKGROUND OF THE INVENTION

This invention relates to a bin for kitchen or other domestic waste, particularly but not exclusively for food or other biodegradable waste materials.

Kitchen bins often comprise an outer casing defining a receptacle for a disposable or removable liner, and an upwardly or inwardly opening lid. Commonly used kitchen bins include a lid which may be opened by actuating a foot pedal. Alternatively the lid may open inwardly against the action of a spring. A problem with kitchen bins is that the relatively high temperature in a kitchen can accelerate the degradation of food waste leading to unpleasant odors which might attract vermin.

SUMMARY OF THE INVENTION

Bins in accordance with this invention may be used for disposal of other domestic waste including bathroom or horticultural waste. However such bins are most commonly used for kitchen waste and are referred to in this specification for simplicity as kitchen waste bins.

An embodiment of the present invention is generally directed toward a kitchen waste bin that includes: a casing defining a receptacle for waste, the receptacle having a mouth; a lid attached to the casing by a hinge and moveable between an open position and a closed position covering the mouth; an actuator arranged to open and close the lid where the lid includes an outer casing, an inner casing and a cavity between the outer and inner casings, the inner casing having one or more apertures communicating between the cavity and the interior of the receptacle when the lid is closed; an ozone generator located within the cavity and arranged to discharge ozone into the receptacle where the ozone generator is an ultraviolet source that includes an elongate lamp disposed in an elongate channel-shaped reflector, the channel-shaped reflector being open at ends thereof, the inner casing having two inlets adjacent the ends of the reflector; a switch arranged to generate a control signal when the lid is moved between the open and closed positions; and a control unit arranged to switch the ozone generator on or off in response to a control signal so that ozone is discharged into the receptacle for a sterilization period when the lid is closed and further arranged to interrupt the discharge when the lid is opened. The ozone generator is typically an ultraviolet radiation source.

Other embodiments may be powered by a battery or main electrical powered supply. Use of a rechargeable battery is preferred.

The use of an ultraviolet ozone generator is preferred since a user is provided with a visual indication that the deodorisation and sterilisation are taking place.

Location of the ozone generator in the cavity of the lid is advantageous to prevent contamination with food waste as it is deposited into or removed from the receptacle.

The control unit is preferably located within the cavity. This conveniently protects the unit from ingress of waste solids or liquid in use.

The lid is preferably mounted on top of the receptacle and opens upwardly to allow access to the receptacle. The lid preferably includes a ventilation circuit comprising an inlet in an inner casing for air from the receptacle, a fan arranged to draw air from the inlet across the ozone generator, and an outlet for discharging ozone enriched air to the receptacle.

The ozone generator is typically an elongated ultra violet lamp, disposed in an elongated channel-shaped reflector. Preferably the reflector has an axis and the lamp is disposed along the axis of the channel of the reflector. The channel-shaped reflector is typically open at both ends, the inner casing having two inlets adjacent the ends of the reflector.

The fan may be located adjacent the outlet. In a preferred embodiment the fan discharges air directly through the outlet into the receptacle. The outlet may comprise a circular array of apertures having a diameter corresponding to the diameter of the fan.

The outlet is preferably located adjacent the centre of the channel of the reflector so that air is drawn in through the inlet along the length of the lamp within the channel and discharged by the fan through the outlet. This configuration increases contact between the air flow and the surface of the lamp and reflector to improve efficiency of ozone generation.

In a preferred embodiment a window is located below the channel so that the interior of the receptacle is illuminated by the lamp. The window and channel may cooperate to form a duct through which air can be drawn across the lamp in use.

In a preferred embodiment the cover is circular in plan view and the channel extends diametrically of the cover.

In a preferred embodiment the receptacle includes a sleeve or bucket which may be removed to allow disposal of waste from the receptacle. A polymeric bin liner may be employed.

The actuator preferably comprises a foot pedal. Alternatively a proximity sensor may actuate an electric motor to open or close the lid.

The power supply may comprise a battery or mains power supply as convenient. Alternatively or in addition the foot pedal may be linked to a piezo electric generator in order to generate a voltage discharge sufficient to form ozone as the lid is opened and closed.

The lid preferably comprises an illuminated display, for example a light emitting diode arranged to be illuminated when the ozone generator is in use.

BRIEF DESCRIPTION OF THE DRAWINGS

The invention is further described by means of example but not in any limitative sense with reference to the accompanying drawings of which.

DETAILED DESCRIPTION OF PREFERRED EMBODIMENT

Figure 1:
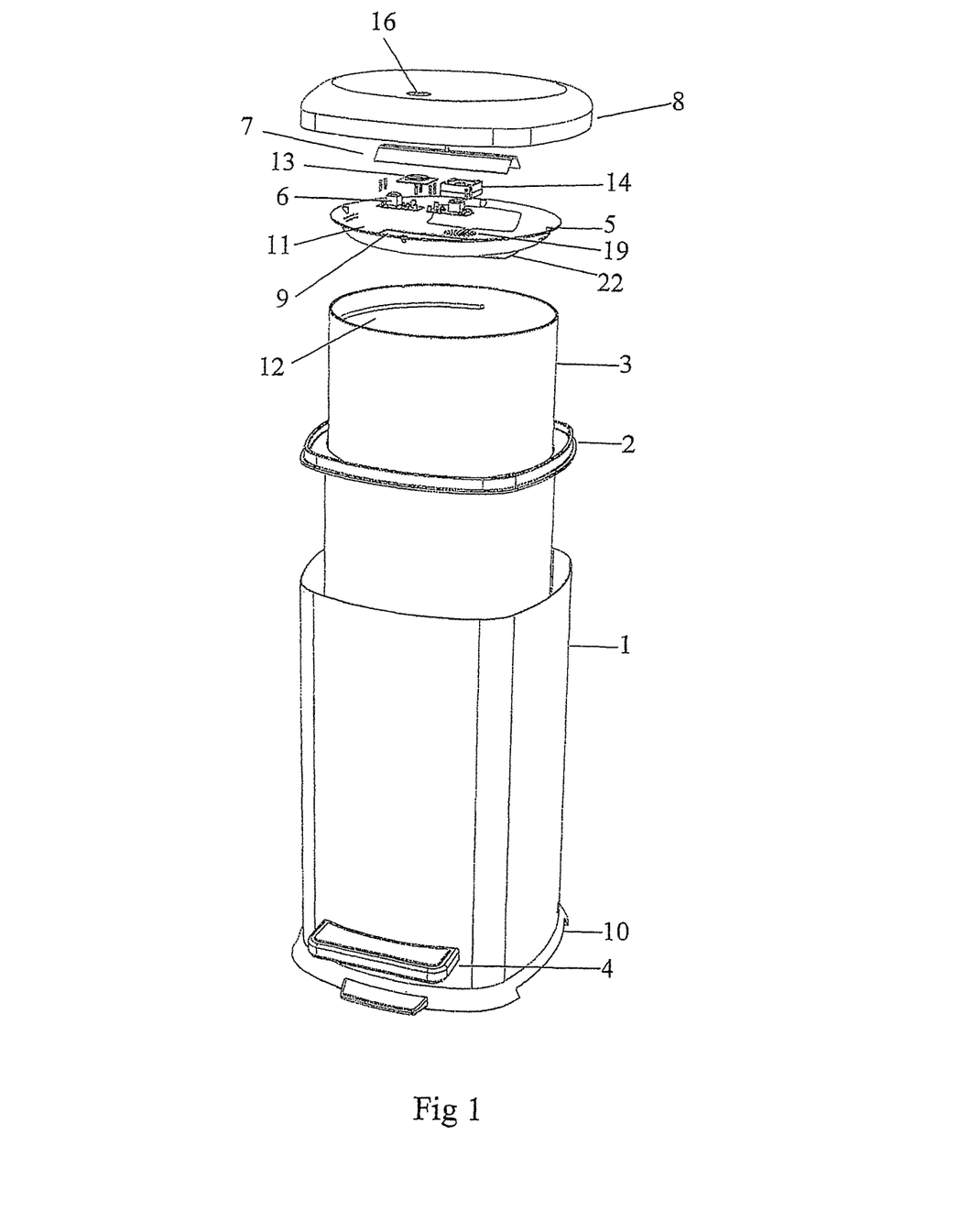
FIG. 1 is an exploded view of a bin in accordance with the invention.

The kitchen waste bin shown in FIG. 1 includes a casing formed from an outer body 1 and an inner sub body 2 having ground engaging foot portion 10 and a foot pedal actuator 4. The sub body 2 defines a generally cylindrical receptacle within which an inner body or sleeve 3 is slidably received. A lid comprises an outer casing or top cap 8 and an inner casing 5. The inner casing has an aperture 9 communicating with a cavity 11 formed between the outer casing 8 and inner casing 5. The outer casing 8 is secured to the outer body 1 using a hinge.

An ultraviolet ozone generating lamp 15 mounted in an elongate downwardly facing reflector 7 transmits UV radiation through the aperture 9 into the cavity 12 within the receptacle. The aperture 9 includes a transparent window 22.

A battery 17 is accessible via a removable panel 20 in the inner cover for recharging or replacement. A fan 14 is mounted on the inner surface of the inner cover generally centrally of the lamp and reflector.

A linkage between the foot pedal 4 and the lid is arranged to cause the lid to open when the foot pedal is depressed. In alternative embodiments the foot pedal may be omitted and the proximity sensor located on the casing 1 adjacent the lid to cause the lid to open when a user's hand moves close to it.

Figure 2:
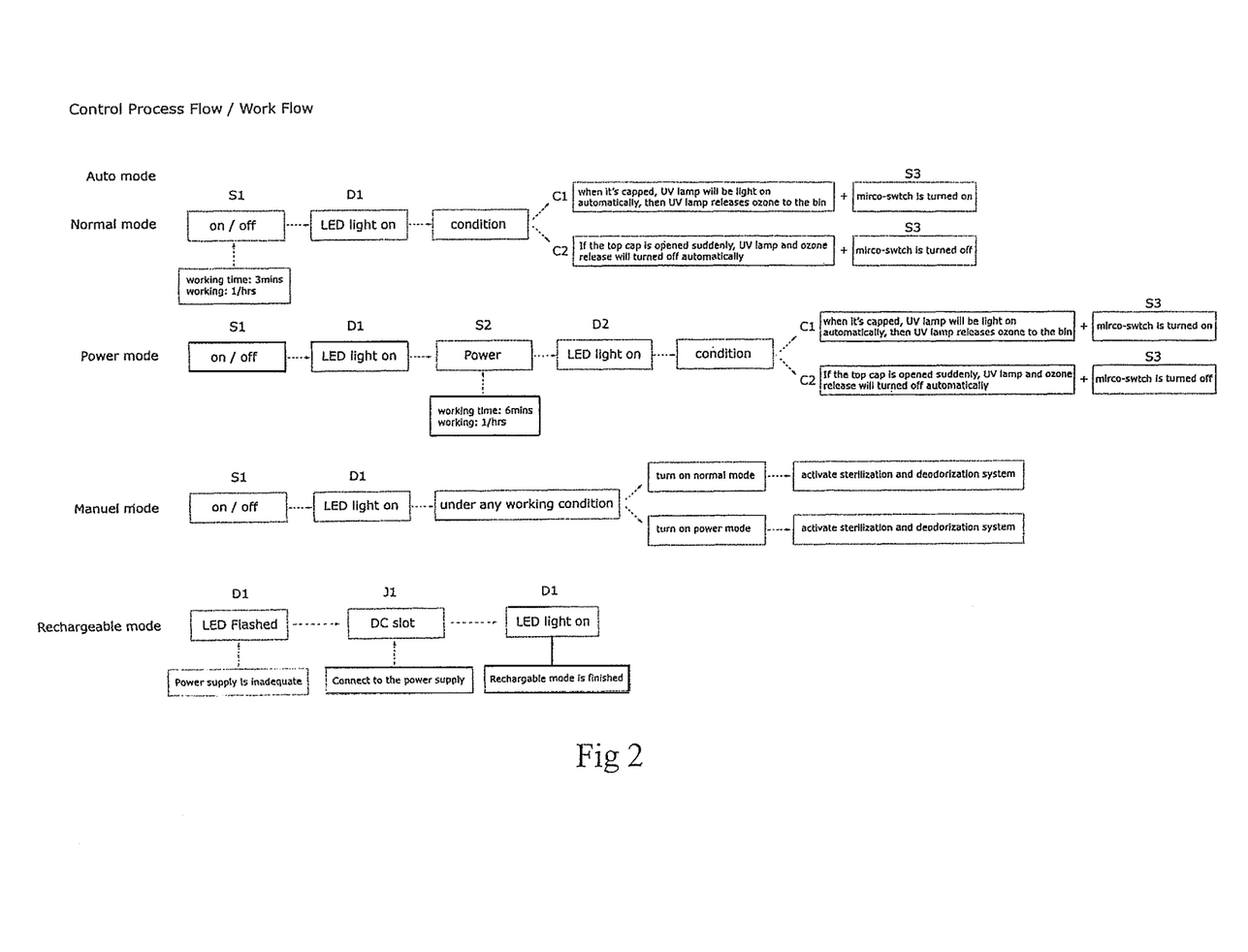
FIG. 2 is a flow chart showing the operation of the bin.

FIG. 2 includes four flow charts for various modes of operation of the kitchen waste bin shown in FIG. 1. In the normal mode an LED display 13 in FIG. 1 projecting through an aperture 16 in the upper casing of the lid indicates the functional condition of the device. When the lid is closed the UV lamp is illuminated releasing ozone through the aperture 19 into the receptacle 12. If the lid is opened suddenly the UV lamp is switched off. In the power mode the UV generator is powered and the LED light 13 illuminated. When the lid is closed the UV light is on releasing ozone into the receptacle. When the lid is opened the UV lamp and ozone release are turned off by the control unit 6. In a manual mode the UV generator can be turned on to sterilize and deodorize the contents of the receptacle 12. In a recharging mode a power supply is connected to the bin recharging the battery. The LED light remains illuminated until charging is complete.

In the normal and power modes the UV light remains illuminated for a sterilisation period following closure of the lid. The sterilisation period may range from 3 minutes to 1 hour and may be set to a predetermined period within this range to meet a users requirements.

Figure 3:
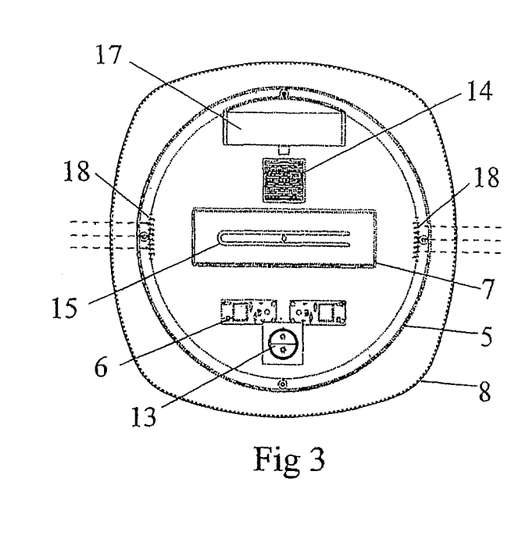
FIG. 3 is a view from underneath the cover.
Figure 4:
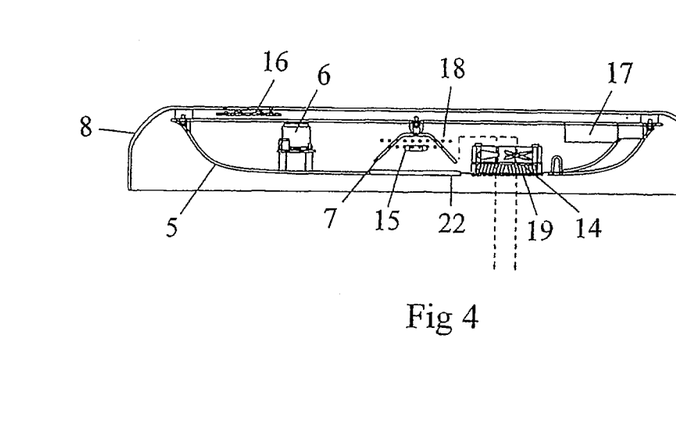
FIG. 4 is a cross section of the cover.

FIGS. 3 and 4 are a view from beneath the lid and a cross sectional view of the lid. An ultraviolet lamp 15 is disposed generally diametrically of the circular inner cover, coaxially with an elongate channel-shaped reflector 7. Inlets 18 are disposed in the inner cover in alignment with the lamp 15 and channel 7 so that air is drawn through the inlets 18 along the length of the lamp 15 within channel 7 by the fan 14. The outlet from the fan 14 comprises a circular array of apertures 19 communicating with the interior of the receptacle in use. The transparent window 22 in aperture 9 allows ultraviolet radiation to illuminate the interior of the receptacle. The window 22 and channel 7 cooperate to form a duct or passageway along which air may pass from the inlet, promoting a generation of ozone.

Figures 5, 6:
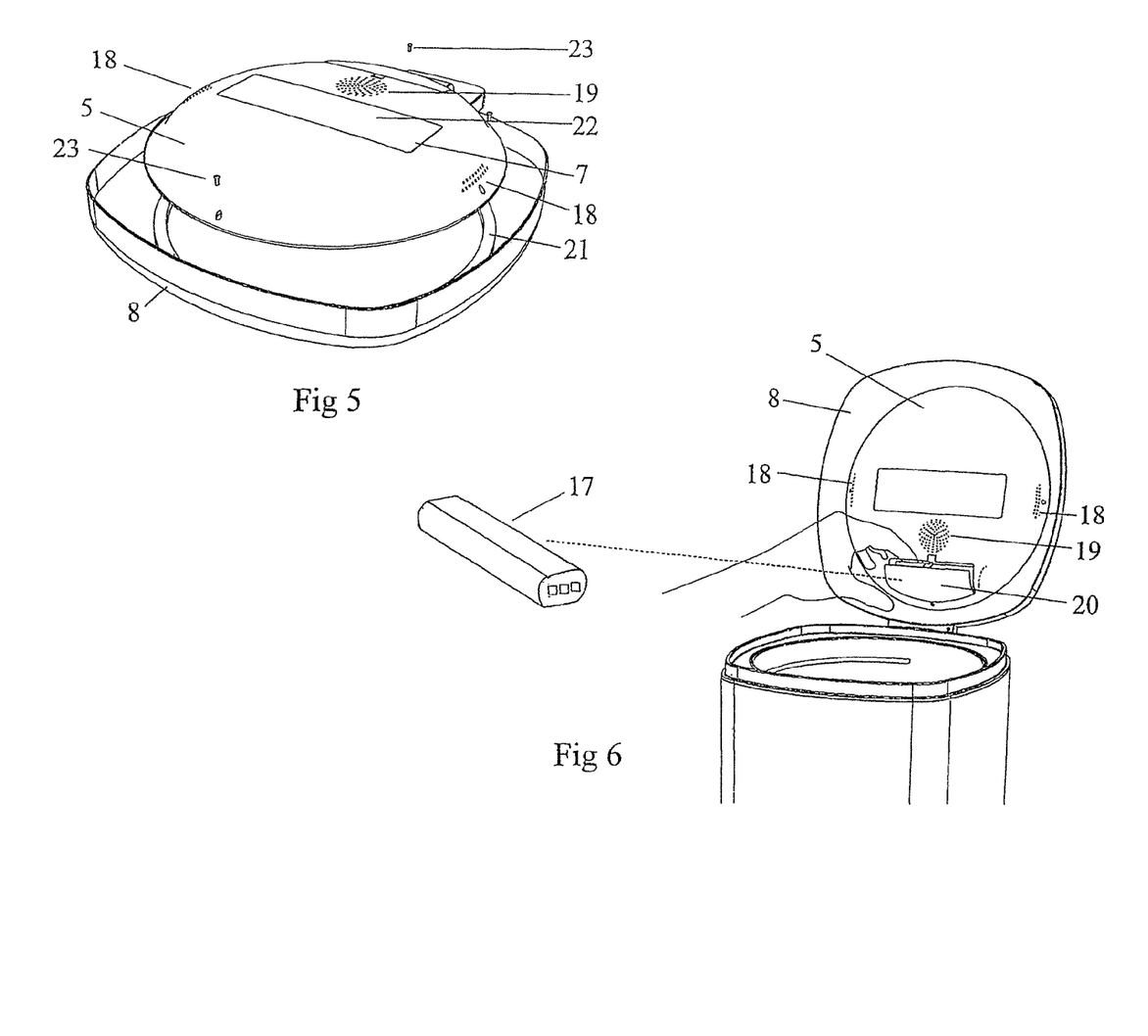
FIG. 5 shows the assembly of the inner and outer covers.
FIG. 6 shows replacement of the battery.

FIG. 5 shows the assembly of the inner cover 5 to the outer cover 8 of the lid. A metal ring 21 soldered to the outer cover 8 may provide a secure fixing for screws 23 during assembly of the apparatus.

A rechargeable battery 17 may be retained within the cavity and accessed by a removable door or panel 20 to facilitate removal of the battery for recharging in an external device.

The invention claimed is:

1. A kitchen waste bin comprising:
   a casing defining a receptacle for waste, the receptacle having a mouth;
   a lid attached to the casing by a hinge and moveable between an open position and a closed position covering the mouth;
   an actuator arranged to open and close the lid;
   the lid including an outer casing, an inner casing and a cavity between the outer and inner casings, the inner casing including one or more apertures communicating between the cavity and the interior of the receptacle when the lid is closed;
   an ozone generator located within the cavity and arranged to discharge ozone into the receptacle; wherein the ozone generator is an elongate ultraviolet lamp disposed in an elongate channel-shaped reflector, the channel-shaped reflector being open at ends thereof and defining a channel, the inner casing having two inlets adjacent the ends of the reflector; and
   a ventilation circuit comprising an inlet in the inner casing for air from the receptacle, a single fan adjacent an outlet, arranged to draw air from the inlet across the ozone generator to produce ozone enriched air, and the outlet located adjacent the center of the lamp and channel, for discharging ozone enriched air to the receptacle.

2. The kitchen waste bin of claim 1, wherein air is drawn in use through the inlets along the channel and discharged by the fan through the outlet.

3. The kitchen waste bin of claim 1, wherein the inner casing includes a window adjacent the lamp to illuminate the interior of the receptacle in use, wherein the window and channel cooperate to form a duct for air to be drawn from the inlet adjacent the lamp.

4. The kitchen waste bin of claim 1, wherein the lid is mounted to open outwardly on the top of the receptacle, a control unit is located within the cavity, and the lid includes an illuminated display.

5. The kitchen waste bin of claim 1, further comprising a switch arranged to generate a control signal when the lid is moved between the open and closed positions; and a control unit arranged to switch the ozone generator on or off in response to the control signal so that ozone is discharged into the receptacle for a sterilization period when the lid is closed and further arranged to interrupt the discharge when the lid is opened.

6. A kitchen waste bin comprising:
   a casing defining a receptacle for waste, the receptacle having a mouth;
   a lid attached to the casing by a hinge and moveable between an open position and a closed position covering the mouth;
   an actuator arranged to open and close the lid;
   the lid including an outer casing, an inner casing and a cavity between the outer and inner casings, the inner casing including one or more apertures communicating between the cavity and the interior of the receptacle when the lid is closed;
   an ozone generator located within the cavity and arranged to discharge ozone into the receptacle; wherein the ozone generator is an ultraviolet source; comprising an elongate lamp disposed in an elongate channel-shaped reflector, the channel-shaped reflector being open at ends thereof, the inner casing having two inlets adjacent the ends of the reflector;

a switch arranged to generate a control signal when the lid is moved between the open and closed positions;

a control unit arranged to switch the ozone generator on or off in response to a control signal so that ozone is discharged into the receptacle for a sterilization period when the lid is closed and further arranged to interrupt the discharge when the lid is opened;

an outlet for discharging ozone enriched air generated by the ozone generator to the receptacle; and a ventilation circuit comprising an inlet in the inner casing for air from the receptacle, a single fan adjacent the center of the lamp and the channel and arranged to draw air from the inlet across the ozone generator to produce ozone enriched air.

7. The kitchen waste bin of claim 6, wherein the lid is mounted to open outwardly on the top of the receptacle, the control unit is located within the cavity and the lid includes an illuminated display.

8. A kitchen waste bin comprising:

a casing defining a receptacle for waste, the receptacle having a mouth and an interior;

a lid attached to the casing by a hinge and moveable between an open position and a closed position covering the mouth;

an actuator arranged to open and close the lid;

the lid including an outer casing, an inner casing and a cavity between the outer and inner casings, the inner casing including one or more apertures communicating between the cavity and the interior of the receptacle when the lid is closed and wherein the lid is mounted to open outwardly on the top of the receptacle and includes an illuminated display that, when activated, illuminates the interior of the receptacle;

an ozone generator located within the cavity and arranged to discharge ozone into the receptacle; wherein the ozone generator is an ultraviolet source; comprising an elongate lamp disposed in an elongate channel-shaped reflector, the channel-shaped reflector being open at ends thereof and defining a channel, the inner casing having two inlets adjacent the ends of the reflector;

a switch arranged to generate a control signal when the lid is moved between the open and closed positions;

a control unit located within the cavity and arranged to switch the ozone generator on or off in response to a control signal so that ozone is discharged into the receptacle for a sterilization period when the lid is closed and further arranged to interrupt the discharge when the lid is opened;

an outlet for discharging ozone enriched air generated by the ozone generator to the receptacle; and wherein air is drawn in use through the inlets along the channel and discharged by the fan through the outlet;

a ventilation circuit comprising an inlet in the inner casing for air from the receptacle; and a fan located adjacent the outlet and arranged to draw air from the inlet across the ozone generator to produce ozone enriched air.

* * * * *

UNITED STATES PATENT AND TRADEMARK OFFICE
CERTIFICATE OF CORRECTION

Page 1 of 1

PATENT NO. : 8,771,606 B2
APPLICATION NO. : 12/840620
DATED : July 8, 2014
INVENTOR(S) : Sun It is certified that error appears in the above-identified patent and that said Letters Patent is hereby corrected as shown below:

In the Specification

Column 1, lines 63 and 64, "deodorization and sterllization" should be --deodorization and sterilization--;

Column 2, line 10, "ultra violet" should be --ultraviolet--;

Column 2, line 23, "centre" should be --center--;

Column 3, line 49, "users" should be --user's--;

Column 3, lines 50 and 51, "cross sectional" should be --cross-sectional--; and

In the Claims

Column 4, Claim 1, line 11, "dosed" should be --closed--.

Signed and Sealed this
Seventeenth Day of February, 2015

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,771,606 B2 | Page 1 of 1 |
| APPLICATION NO. | : 12/840620 | |
| DATED | : July 8, 2014 | |
| INVENTOR(S) | : Sun | |

It is certified that error appears in the above-identified patent and that said Letters Patent is hereby corrected as shown below:

On the Title Page, Item (57) Abstract, delete "there between" and replace with --therebetween--.

Signed and Sealed this
Twenty-sixth Day of May, 2015

Michelle K. Lee
*Director of the United States Patent and Trademark Office*